United States Patent
Carstens

(10) Patent No.: US 7,235,108 B2
(45) Date of Patent: Jun. 26, 2007

(54) PROSTHESIS LINER OR SOCKET WITH A SEAL AT THE DISTAL END

(75) Inventor: Felix Carstens, Neustadt an der Weinstrasse (DE)

(73) Assignee: Ossur HF, Reykjavik (IS)

( * ) Notice: Subject to any disclaimer, the term of this patent is extended or adjusted under 35 U.S.C. 154(b) by 525 days.

(21) Appl. No.: 10/487,925

(22) PCT Filed: Oct. 31, 2002

(86) PCT No.: PCT/DE02/04059

§ 371 (c)(1),
(2), (4) Date: Feb. 27, 2004

(87) PCT Pub. No.: WO03/039398

PCT Pub. Date: May 15, 2003

(65) Prior Publication Data

US 2004/0243251 A1     Dec. 2, 2004

(30) Foreign Application Priority Data

Nov. 5, 2001    (DE) ............................. 101 53 796

(51) Int. Cl.
*A61F 2/78* (2006.01)
(52) U.S. Cl. .......................................... 623/36; 623/34
(58) Field of Classification Search .............. 623/34, 623/36, 37, 33
See application file for complete search history.

(56) References Cited

U.S. PATENT DOCUMENTS

| | | | |
|---|---|---|---|
| 980,457 A | 1/1911 | Toles | |
| 1,398,824 A | 11/1921 | Abrams | |
| 1,893,853 A | 1/1933 | Tullis | |
| 2,530,285 A | 11/1950 | Catranis | |
| 2,533,404 A | 12/1950 | Sharp et al. | |
| 2,634,424 A | 1/1953 | O'Gorman | |
| 2,671,225 A | 3/1954 | Schoene et al. | |
| 2,808,593 A | 10/1957 | Andersen | |
| 3,393,407 A | 7/1968 | Kandel | |
| 3,671,980 A | 6/1972 | Baird | |
| 4,923,474 A | 5/1990 | Klasson et al. | |
| 5,007,937 A | 4/1991 | Fishman et al. | |
| 5,139,523 A | 8/1992 | Paton et al. | |
| 5,163,965 A | 11/1992 | Rasmusson et al. | |
| 5,226,918 A | 7/1993 | Silagy et al. | |
| 5,314,496 A | 5/1994 | Harris et al. | |
| 5,376,129 A | 12/1994 | Faulkner et al. | |
| 5,376,131 A | 12/1994 | Lenze et al. | |
| 5,549,709 A | 8/1996 | Caspers | |

(Continued)

FOREIGN PATENT DOCUMENTS

DE    745 981    12/1943

(Continued)

*Primary Examiner*—David H. Willse
(74) *Attorney, Agent, or Firm*—Bacon & Thomas, PLLC

(57) ABSTRACT

A prosthetic liner for receiving a residual limb has a body with an open proximal end and a closed distal end. The liner includes a seal having an annular sealing lip positioned about the body axis on the body distal end. The sealing lip includes a root that is secured to the body distal end, and a sealing edge that extends from the root so as to form an opening and is biased away from the body distal end.

12 Claims, 6 Drawing Sheets

U.S. PATENT DOCUMENTS

| | | | |
|---|---|---|---|
| 5,593,454 A * | 1/1997 | Helmy | 623/32 |
| 5,658,353 A | 8/1997 | Layton | |
| 5,662,715 A * | 9/1997 | Slemker | 623/36 |
| 5,702,489 A | 12/1997 | Slemker | |
| 5,718,925 A | 2/1998 | Kristinsson et al. | |
| 5,728,170 A | 3/1998 | Becker et al. | |
| 5,735,906 A | 4/1998 | Caspers | |
| 5,888,216 A | 3/1999 | Haberman | |
| 5,904,722 A | 5/1999 | Caspers | |
| 5,931,872 A | 8/1999 | Lohmann | |
| 5,972,036 A | 10/1999 | Kristinsson et al. | |
| 6,149,691 A | 11/2000 | Fay et al. | |
| 6,231,616 B1 | 5/2001 | Helmy | |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,361,568 B1 | 3/2002 | Hoerner | |
| 6,508,842 B1 | 1/2003 | Caspers | |
| 6,554,868 B1 | 4/2003 | Caspers | |
| 6,585,774 B2 | 7/2003 | Dean, Jr. et al. | |
| 6,645,253 B2 | 11/2003 | Caspers | |
| 6,726,726 B2 | 4/2004 | Caspers | |
| 6,761,742 B2 | 7/2004 | Caspers | |
| 2001/0005798 A1 | 6/2001 | Caspers | |
| 2001/0016781 A1 | 8/2001 | Caspers | |
| 2002/0040248 A1 | 4/2002 | Karason | |
| 2002/0087215 A1 | 7/2002 | Caspers | |
| 2002/0091449 A1 | 7/2002 | Caspers et al. | |
| 2002/0099450 A1 | 7/2002 | Dean, Jr. et al. | |
| 2003/0191539 A1 | 10/2003 | Caspers | |
| 2004/0030411 A1 | 2/2004 | Caspers | |
| 2004/0098136 A1 | 5/2004 | Caspers | |
| 2004/0122528 A1 | 6/2004 | Egilsson | |
| 2004/0143345 A1 | 7/2004 | Caspers | |
| 2004/0167638 A1 | 8/2004 | Caspers | |
| 2004/0181290 A1 | 9/2004 | Caspers | |
| 2004/0236434 A1 | 11/2004 | Carstens | |
| 2004/0243251 A1 | 12/2004 | Carstens | |

FOREIGN PATENT DOCUMENTS

| | | |
|---|---|---|
| DE | 813190 | 7/1951 |
| DE | 1795809 | 9/1959 |
| DE | 2060239 A1 | 6/1972 |
| DE | 2540138 A1 | 3/1977 |
| DE | 3221920 | 4/1983 |
| DE | 3508919 A1 | 9/1986 |
| DE | 9419208.1 | 11/1994 |
| GB | 267988 | 3/1927 |
| GB | 2 069 847 | 9/1981 |
| GB | 2 087 727 | 6/1982 |
| JP | 7155343 A | 6/1995 |
| WO | 00/74611 A2 | 12/2000 |
| WO | 01/54631 | 8/2001 |
| WO | 03/099173 A1 | 12/2003 |

* cited by examiner

PROSTHESIS LINER OR SOCKET WITH A SEAL AT THE DISTAL END

BACKGROUND

A. Field of the Invention

This invention relates to prosthesis liner or socket having a seal at its distal end.

B. Related Art

With prostheses in general and leg prostheses in particular, a substantial effort is made to spread the retention force with which the prosthesis is attached to the involved residual limb over as large a surface as possible. So-called suction prostheses are especially advantageous in that respect, as they are sealed hermetically against the residual limb. When a force occurs tending to pull the prosthesis off the residual limb, a partial vacuum is produced which, in cooperation with the external atmospheric pressure, retains the prosthesis on the residual limb.

The suction socket presumes a positive air tight seal. When leaks arise, the partial vacuum at once disappears and the residual limb slips out of the socket.

It is clear on its face that such an event occuring with a leg prosthesis entails a dangerous fall. If the patient during walking loses the prosthesis, his/her step cannot be completed because the affected leg is suddenly shortened. Because walking/running is a dynamic process, the patient has no chance of stopping the step short.

Heretofore, one-hundred percent reliable air tight seals could not be assured. The residual limb volume changes with the patient's blood pressure, the temperature, and the like in such a way that a socket which is well-fitting and air tight one day may be poorly fitting and very loose another. The resulting consequence is the danger discussed above.

In order to safely preclude such danger, liners pulled over the residual limbs are used for prosthetic sockets, even those that are for above-knee use. At its distal end the liner is fitted with a locking adapter engaging a detent mechanism or the like of the prosthetic socket. In this configuration the liner is seated in an air tight manner on the residual limb and there is no danger of the residual limb slipping out of the liner. Moreover, on account of its intrinsic prestressing force, the liner is frictionally held against the residual limb. On the other hand the liner's elasticity results in strong narrowing at its distal end when tension is introduced at such end through the locking adapter. The result is a so-called milking effect.

It is important for comfort during wearing that the residual limb not be compressed when a tension is applied to the distal end. Such objective may be assured when the liner is inserted in the hard prosthetic socket in an air tight condition and is kept there by means of a partial vacuum.

Accordingly, those embodiments which involve both mechanical and hermetic attachment will be advantageous.

In another example, the liner should include assistance for inserting the liner into a socket. For that purpose the liner is fitted at its distal end with a cord which initially is threaded through an aperture at the prosthetic socket distal end. The patient forcefully pulls the cord through the aperture, such that the residual limb, seated in the liner, is pulled into the prosthetic socket. Thereupon the cord is secured on the outside of the prosthetic socket. In this kind of prosthesis, the prosthetic socket is retained against the residual limb substantially by friction in relation to the cord affixed on the outside of the prosthetic socket.

BRIEF SUMMARY OF THE INVENTION

As compared to the above discussed state of the art, the objective of the present invention is to create a prosthetic socket assuring reliable retention by partial vacuum even when the prosthetic socket has openings at its distal end.

Another objective of the present invention is to create a residual limb liner which is fitted with a locking adapter or a cord and which nevertheless can be held firmly in the prosthetic socket by partial vacuum.

All prosthetic sockets fitted with additional mechanical liner locks share the characteristic of a more or less air leakage through larger or smaller openings in the distal end of the socket. Air can move through these openings into the prosthetic socket into the gap between the socket's inside wall and the liner. If so, the partial vacuum then collapses and the prosthetic socket can hardly be retained on the liner. To prevent such leakages, all embodiments of the present invention provide a substantially annular seal fitted with a sealing lip running around the opening. The sealing lip subtends a sealing edge that is nearer the opening than its root.

Depending on the type of embodiment involved, the seal may be affixed by its root to the prosthetic socket's inner side, or it may be affixed to the outside of the liner at the locking adapter.

When the prosthetic socket is loaded in tension, external air flows through the prosthetic socket aperture into the gap between the liner and socket. As a result a pressure gradient is created at the sealing edge that will compress the edge ever more strongly against the liner or the prosthetic socket the greater the differential is between the pressure in the prosthetic socket's gap and the external atmospheric pressure. Sealing may always be assured even when initially the sealing edge rests by means of a small prestressing force against the respective opposed surface, namely the liner or the prosthetic socket, depending on where the seal is not hermetically sealed at its root.

If the prosthetic socket is fitted with an annular, disk type seal the root of which is integral, air tight bonded with the socket, various types of liners may be used. Liners may be used wherein a cord is provided at their distal end that is pulled through the opening, and liners may be used which are designed with rigid locking adapters using pins or the like. The seal may be selected to be of very large diameter, so that the danger of damaging the sealing lip by the pin of the locking adapter is precluded. Again, strong prestressing of the seal, sometimes found in the prior art, is not required.

Accordingly the seal in the prosthetic socket offers long service life and also is very reliable compared to O-rings that rest against the smooth part of the pin-shaped locking adapter. The air tightness of such O-rings actually cannot be tested and each time the locking adapter is inserted through the O-rings, they are degraded another bit.

Another approach is to fit the seal with a further sealing edge, both sealing edges then being situated on the same side of the annular root relative to the radial direction of the root. Such a seal is appropriate for retrofitting combinations of liner and prosthetic socket and using pin type locks. The seal may be affixed to the pin and will seal it by a sealing edge. The seal remains on the pin and need not be pierced when the patient enters the prosthetic socket. In this manner any danger of damaging the other sealing edge when the patient enters the prosthetic socket of the invention is precluded.

The basic principle of the present invention also may be applied to liners. In this case the seal is affixed by its root to the liner outer side, and the sealing edge, as before, extends toward the aperture. In this design the sealing edge seals off the aperture at the smooth inner side of the prosthetic socket. Lastly, the basic concept of the invention may be applied to those liners with a cord that is pulled through a prosthetic socket aperture, such liners initially primarily acting as slip-in aids. Said lip in this design even may be made integral with the liner or it may be retro-attached onto the liner.

The last-mentioned approach is especially suitable when replacing prosthetic sockets lacking a seal and liners fitted with draw cords.

It may be appropriate as regards all embodiments to use spacers to ensure the sealing lip rests securely against the surface to be sealed off and from which it will separated when the prosthesis is removed, while involving a low prestressing force. Accordingly the spacers are situated between the sealing lip and the surface to which the root is attached.

Further refinements of the present invention are the objects of the dependent claims. Even those combinations of features that are not explicitly illustrated in discussions of the exemplary embodiments should be construed as being claimed.

DESCRIPTION OF THE DRAWINGS

The drawing shows illustrative embodiments of the present invention.

DETAILED DESCRIPTION

Figure 1:
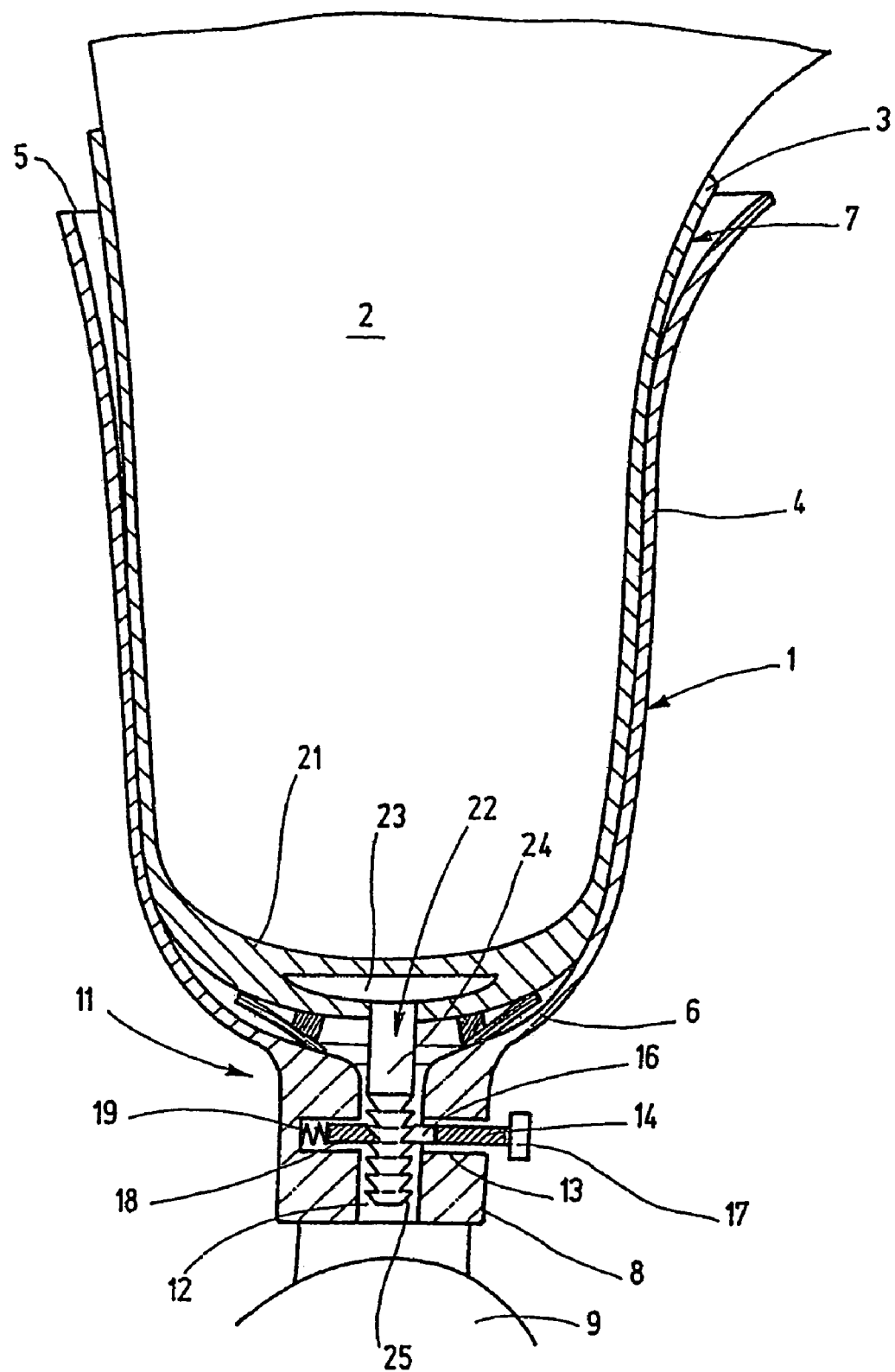
FIG. 1 is a longitudinal section of a residual limb fitted with a liner of the invention operating with a prosthetic socket.

In highly schematic form, and as an example of the present invention, FIG. 1 shows a prosthetic socket 1 for use above-the-knee, into which an amputation residual limb 2 onto which a liner 3 was donned has been received.

The prosthetic socket 1 has a cup-shape configuration comprising a lateral wall 4 subtending an opening 5 at its proximal end and being closed by an inverted dome-like base 6 at its distal end. The wall 4 and the base 6 merge integrally into each other and define a corresponding inner volume 7 that receives the amputation residual limb 2.

At its lower end, the base 6 is integrally extended by a cylindrical fitting 8 connected to an artificial knee 9.

A two-part lock 11 assures reliable and mechanical retention of the liner 3 in the prosthetic socket 1. The lock 11 is fitted with a cylindrical borehole 12 which is located in the cylindrical extension 8 and which at its upper end and through a conically widening opens into the inner volume 7 of the prosthetic socket 1. A passage 13 runs transversely to the cylindrical borehole 12 and receives a longitudinally displaceable slider 14. The passage 13 runs transversely to the longitudinal axis of the borehole 12 and as a result the slider 14 is guided transversely, or radially, relative to the borehole 12. The slider 14 includes an aperture 16 which is fitted on an edge opposite the drive knob 17 with a detent edge 18. The slider 14 is biased by a helical compression spring 19 toward the drive knob 17.

Using stop elements (omitted), the slider 14 can only be advanced a given distance by the helical compression spring 19 toward the drive knob 17. Moreover the stop element (omitted) assures that adequate free space shall remain between the edge of the tooth 18 and the opposite wall of the cylindrical borehole 12.

The liner is a sock-like or pouch-like structure made of an air-impermeable, skin-compatible material such as silicone, having a reinforced base 21 at its distal end. An umbrella-shaped locking element 22 is anchored in the base 21 and constitutes the other part of the locking adapter 11.

The locking element 22 comprises an enlarged head 23 molded into the base 21 as shown. The head 23 is fitted with a cylindrical pin 24 which is smooth in its segment 25 directly adjoining the head 23. The pin 24 is fitted with circumferentially symmetrical serrated teeth 26 at a distance located away from the head 23, said teeth comprising of a plurality of annular adjacent grooves extending along the pin 24. The shapes of the serrated teeth 26 match that of the detent edge 18 and as a result the detent connection described below may take place. Moreover the diameter of the pin 24, i.e. its tapered free end, is selected in such a way that without interference from the slider 14, the pin 24 can be inserted through the borehole 12 and through the aperture 16 of the slider 14.

Figure 2:
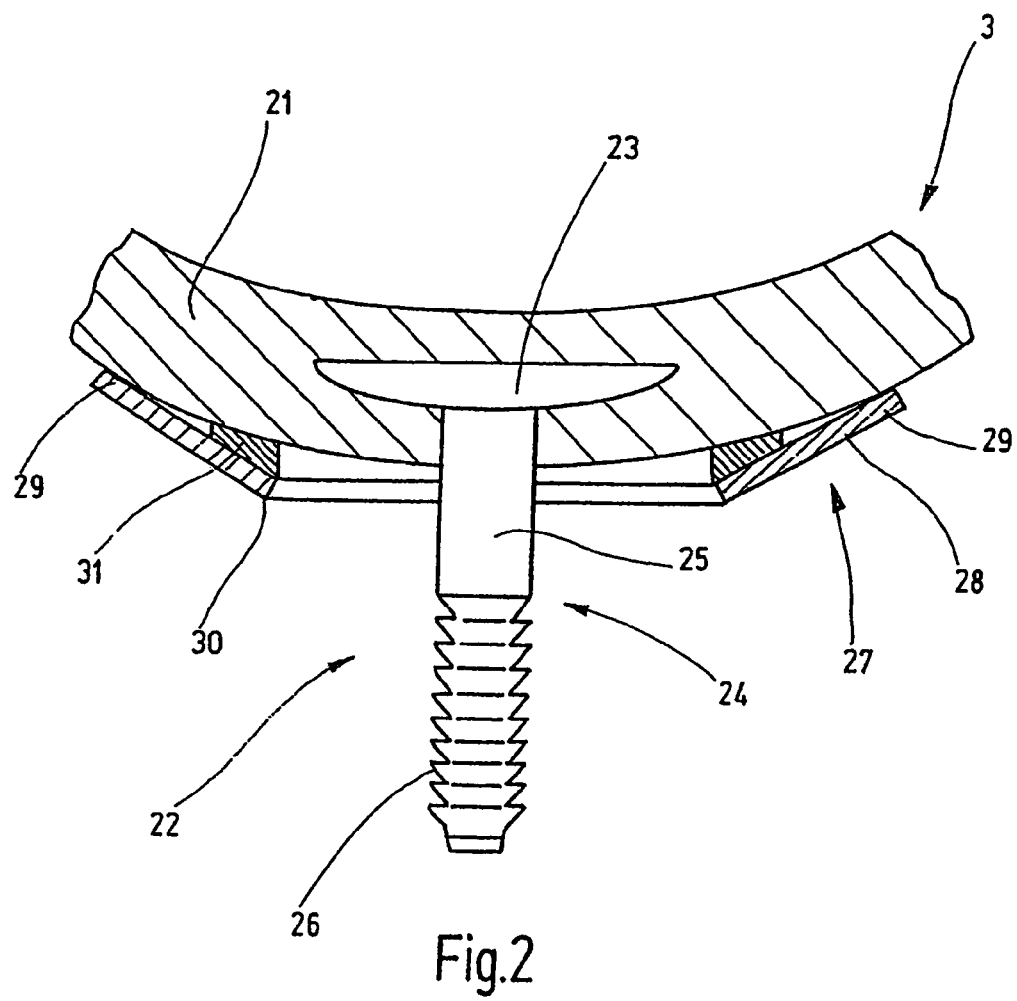
FIG. 2 is an enlarged detail of the distal end of the liner of FIG. 1.

As shown in the enlargement of FIG. 2, a seal 27 is configured on the outside of the base 21. The seal 27 is an elastomeric, substantially circular sealing lip 28. The sealing lip 28 subtends a root 29 and a sealing edge 30. The root 29 is illustratively bonded in an air tight manner to the outside of the base 21. From there the sealing lip 28 projects radially with its sealing edge 30 extending toward the locking pin 24. The sealing edge 30 closes on itself and defines an aperture having a diameter of about 15 to 60 mm, as a result of which the shank 24 is surrounded in all directions by the sealing edge with radial play.

With the use of an annular foam insert 31, the sealing edge 30 is biased a slight distance away from the outside of the base 21. The foam insert 31 is open cell and situated in the gap between the sealing lip and the outside of the base 21.

The configuration discussed above operates as follows:

When the user wants to wear the prosthetic socket and affix it to his residual limb 2, he first will don the liner 3. Upon full insertion into the liner, the end of the residual limb 2 rests against the inside of the base 21. The locking pin 24 then extends in the axial direction of the residual limb 2. Next, with the pin 24 in front, the patient inserts the residual limb 2 into the prosthetic socket 1. During this insertion, the cylindrical pin 24 is trapped by the conical, upper portion of the borehole 12 and is then guided into the borehole 12. During further insertion of the residual limb 2 into the prosthetic socket 1, the pin 24 by its circumferentially symmetrical serrated teeth 26 penetrate and pass through the aperture 16 of the slider 14.

The prosthetic socket 1 will be fully in place as soon as the base 21 of the liner 3 rests on the inside of the base 6 of the prosthetic socket 1. In this condition the sealing edge 29 hermetically rests against the opposite smooth inner side of the prosthetic socket 1. At the same time the pin 24 shall be locked with slider 14 by a corresponding mutual engagement.

If during this operational condition a tension is exerted on the prosthetic socket 1 and axial play exists between the slider 14 and a serration 26, then it will be nevertheless impossible to pull the prosthetic socket 1 off the residual limb 2. As long as the tension is applied, external, atmospheric air will flow through the borehole 12 or the guide duct 13 into inside volume 7 of the prosthetic socket 1. This air reaches the conical gap between the sealing lip 28 and the outside of the base 21 of the liner 3. This air increases the pressure at which the sealing edge 30 is forced against the inside of the prosthetic socket 1, thus strengthening sealing. Due to the sealing edge 30, the air is impeded from penetrating the gap between the liner 3 and the prosthetic socket 1 beyond the sealing lip 28. The above-knee residual limb 2 jointly with its donned liner 3 is retained in place independently of the locking device 11 in the prosthetic socket 1.

The above discussion assumes that the residual limb 2 is seated in sealed manner in the socket 1 at the proximal end. If it were otherwise, an additional and corresponding seal must be provided—which however is not an object of the present invention.

The initially mentioned milking effect cannot occur. The residual limb 2 is held in a dimensionally stable manner within the rigid prosthetic socket 1. No tension forces are transmitted through the pin 24 into the base 21 of the liner 3 that might cause narrowing of the liner 3.

In order to reliably preclude such force transmittal through the pin 24, the serrations 26 may be provided at the tip area only of the pin 24 and the pin segment above may merge into a smooth zone of lesser diameter before reaching the section 25. In this manner the pin 24 would be provided with a commensurate axial play in the slider 14 and would not impede the locking of the prosthetic socket 1 by means of partial vacuum. With such a design of the pin 24, the partial vacuum would become effective first, before the liner 3 might distend due to a force transmitted through the pin 24.

It is easily seen that the sealing lip 28 is directed in such a way that the pressure gradient generated when tension is exerted on the prosthetic socket 1 increasingly compresses the sealing lip 28 against the prosthetic socket 1 the greater the tension and that the partial vacuum would be exerted on the other side of the sealing lip 28.

In order that enough prestressing force be present from the beginning and to assure that the external atmospheric pressure may attain the self-reinforcing compression effect level, use is made of a foam ring 31, which is open-cell.

To allow removing the residual limb 2 out of the prosthetic socket 1, the user opens a valve in the socket 1 to let air flow into the inside space 7 while bypassing the seal 27. After pressing the actuator knob 17, the snap-in serration 26 is released and the residual limb then may be pulled out of the prosthetic socket 1 jointly with the liner 3.

Figure 3:
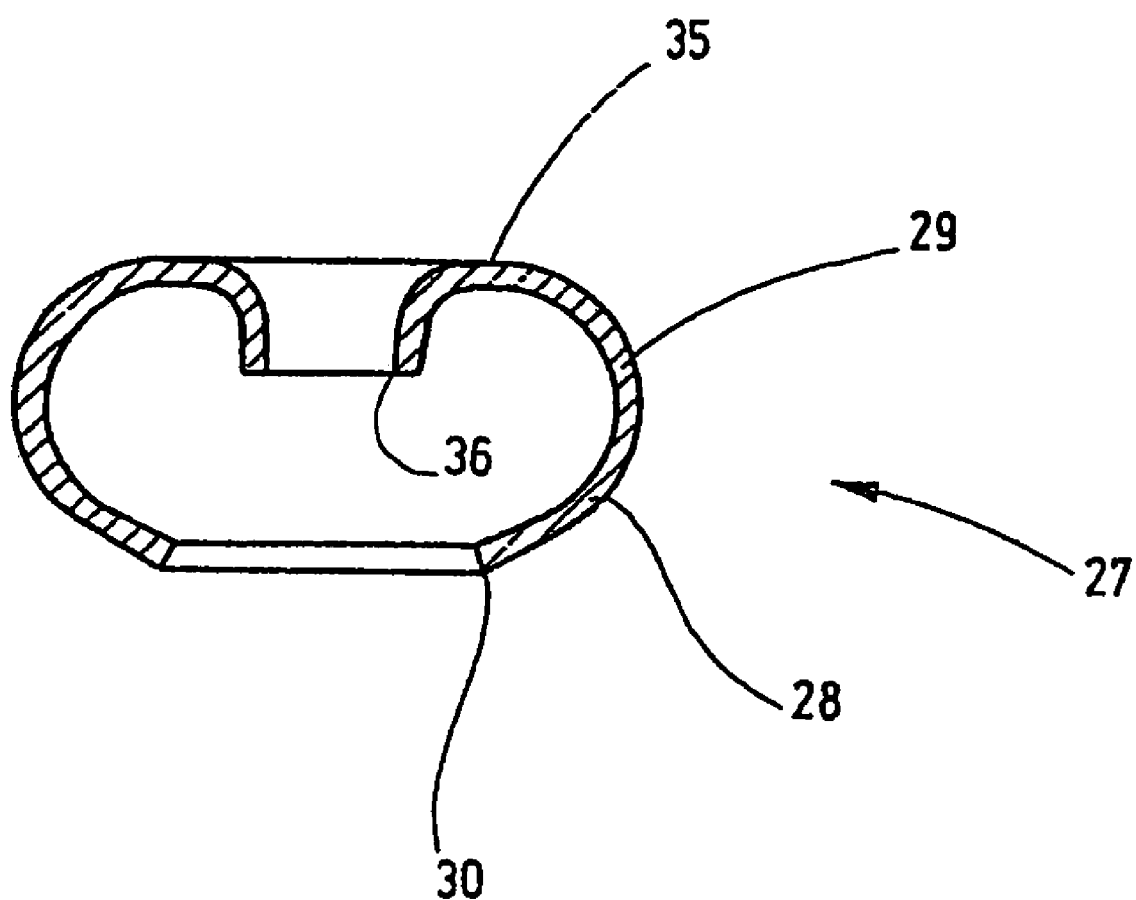
FIG. 3 is another embodiment of a seal for the liners of FIGS. 1 and 2.

Instead of using a flat element as a seal 27 in FIG. 2 that is bonded at its root 29 to the outside of the liner 3, the seal 27 may be configured as shown in FIG. 3.

The seal of FIG. 3 extends beyond the root 29 into a further sealing lip 35 tubularly folding on itself and defining another sealing edge at 36. The two sealing edges 30 and 36 are situated on the same side relative to the root 29 and are located radially relative to an axis passing through the circles defined by the two sealing edges 30 and 36. The seal 27 of FIG. 3 is pulled on the pin 24 and by its sealing edge 36 seals off the smooth, cylindrical segment 25 of the shank 24. Operation of the seal 27 otherwise is as fully described above.

The seal 27 is easily applicable for retrofitting existing liner systems.

Figure 4:
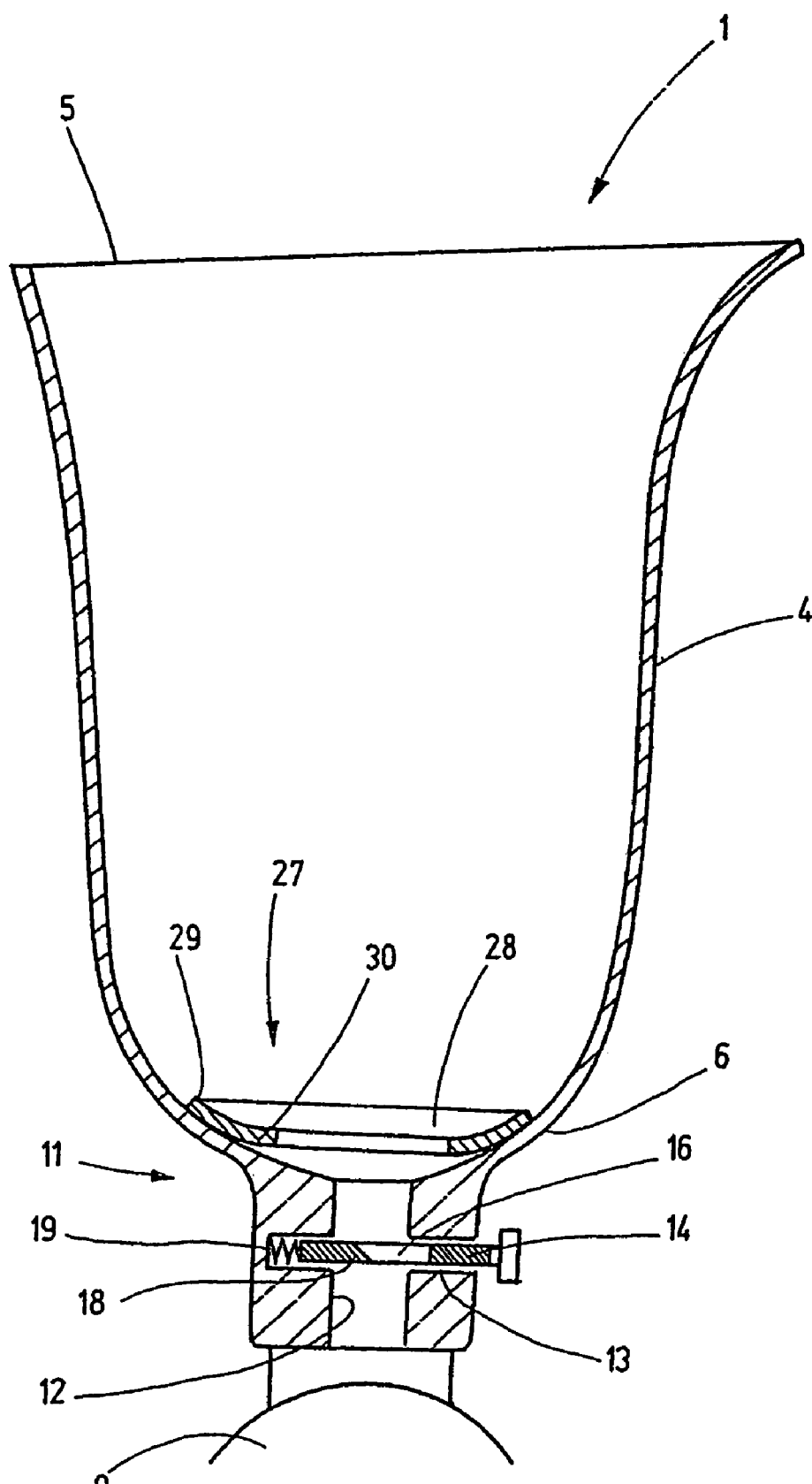
FIG. 4 is a longitudinal section of a prosthetic socket of the invention for a liner with a locking adapter.

FIG. 4 shows an embodiment wherein the seal 27 is adhesively bonded onto a prosthetic socket 1. The geometry of the prosthetic socket 1 of FIG. 4 is identical with that shown in FIG. 1. The liner used in the latter case also is identical with the liner 3 discussed in relation to FIGS. 1 and 2, except that the seal 27 is not bonded to the liner 3. The annular seal 27 instead is hermetically affixed, for instance adhesively, by its root 29 to the inside of the prosthetic socket 1, the sealing edge 30 in this manner defining an aperture concentric with the borehole 12.

Because of the curvature of the base 6 of the socket 1, the seal 27 by its sealing edge 30 will be raised off the inside of the socket 1.

The seal 27 otherwise operates as described above.

Figure 5:
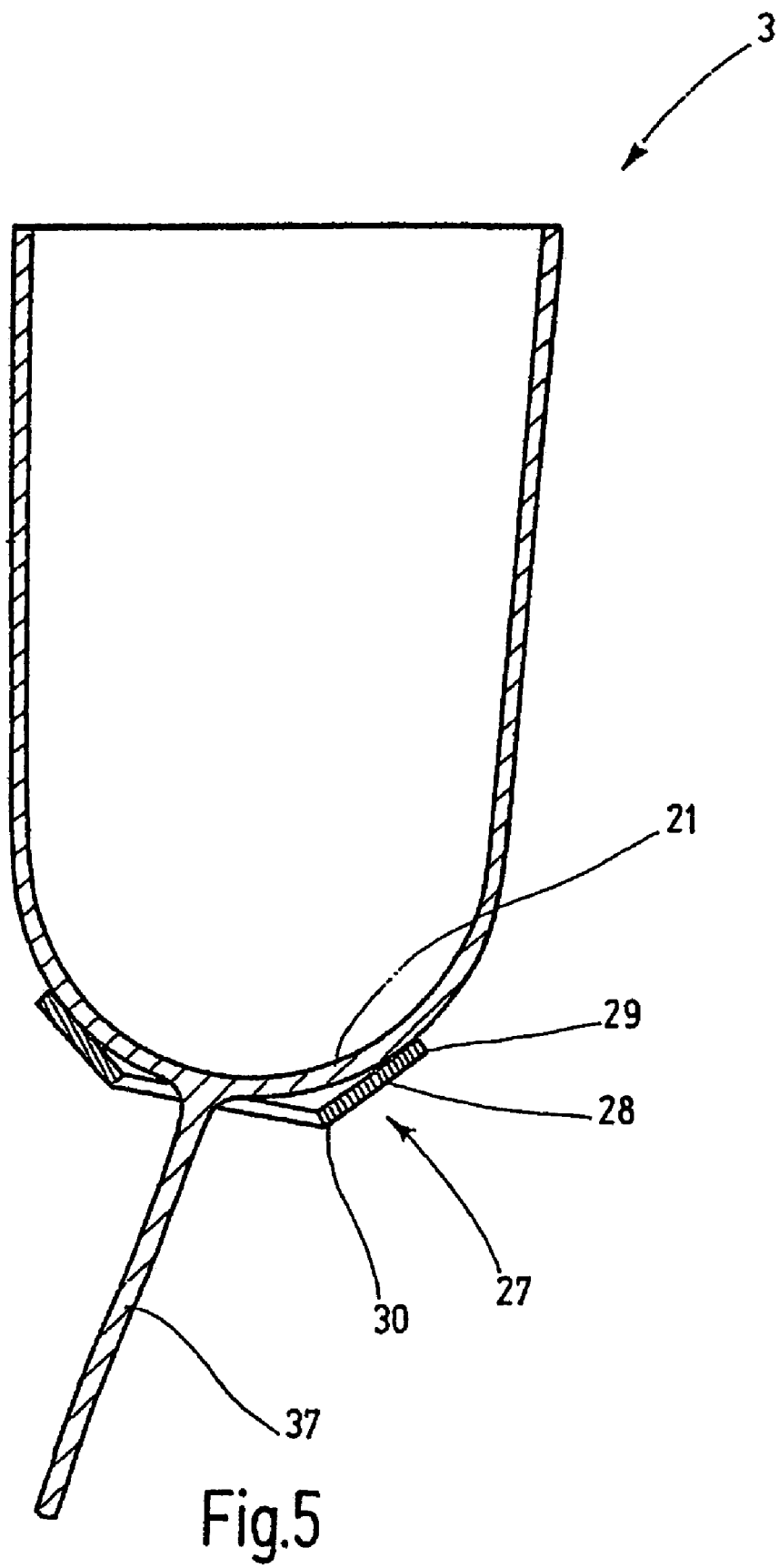
FIG. 5 is a longitudinal section of a liner having a cord for drawing it into a prosthetic socket.

FIG. 5 shows a liner 3 which is fitted at its distal end with a cord 37. Again, an annular seal 27 similar to that of FIG. 2 is adhesively bonded to the outside of the distal base 23 of the liner 3. The liner 3 of FIG. 5 is used with a prosthetic socket such as shown in FIG. 6.

Figure 6:
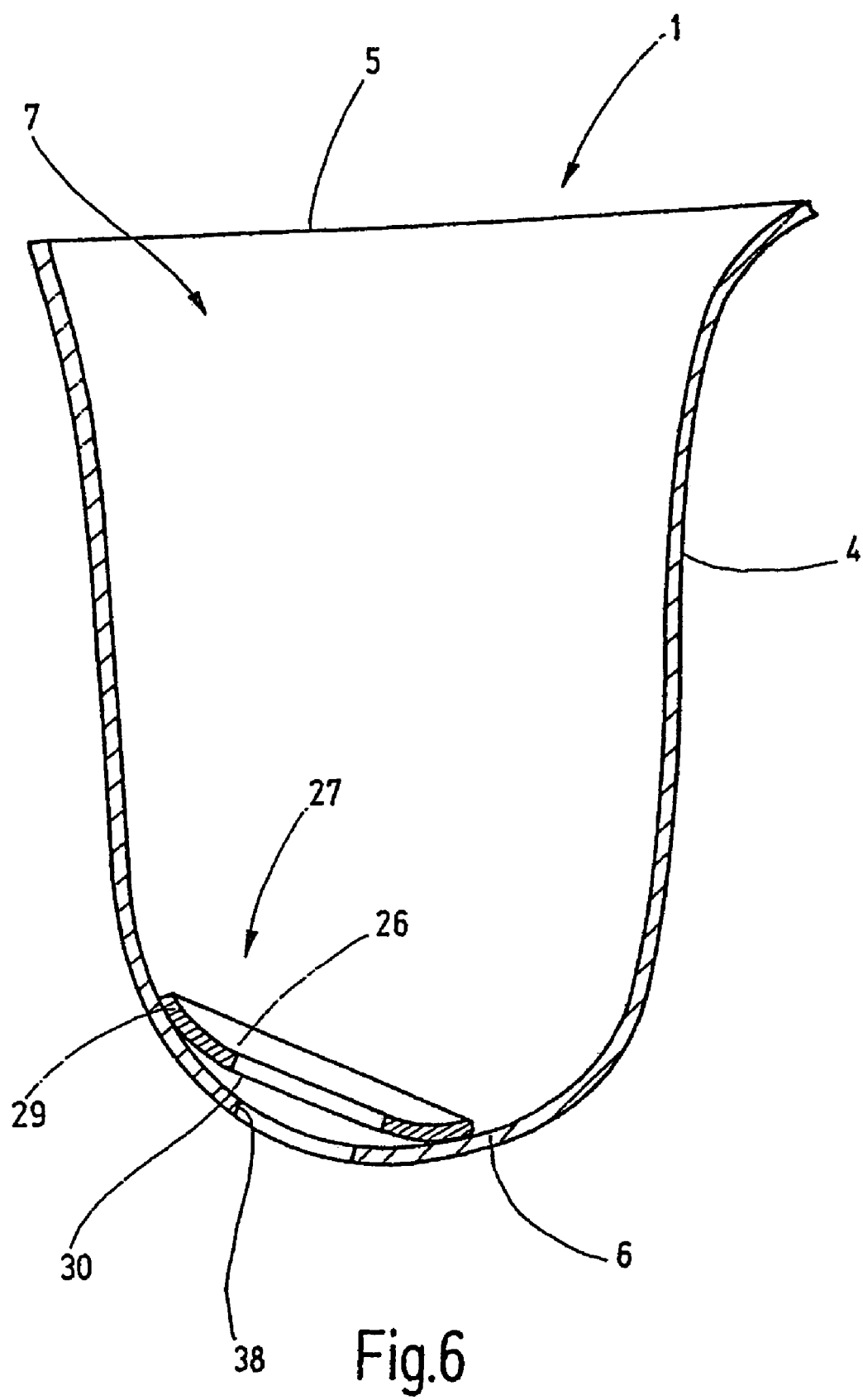
FIG. 6 is a prosthetic socket for the liner of FIG. 5.

The prosthetic socket 1 of FIG. 6 is fitted at its distal end with an aperture 38 through which the cord 37 extends.

When putting on the prosthesis 1, the cord 37 is threaded through the aperture 38. The cord 37 is pulled to assist in inserting the residual limb 2 into the prosthetic socket 1. When fully installed, the sealing edge 30—as already discussed above—will rest against the inside of the prosthetic socket 1. As a result and on account of the partial vacuum, the prosthetic socket 1 is affixed against the outside of the liner 3. Moreover, for mechanical securing, the cord 37 is anchored on a hook (omitted) at the outside of the prosthetic socket 1.

Instead of mounting the seal 27 on the outer side of the liner 3 as shown in FIG. 5, it may also be mounted, as shown in FIG. 6, on the inner side of the prosthetic socket 1. Said seal then is configured concentrically with the aperture 38, its root 29 being adhesively bonded to the inner side of the prosthetic socket 1.

Lastly, a seal 27 on the liner 3 as shown in FIG. 5 may be combined with a seal 27 on the inside of the prosthetic socket 1 as shown in FIG. 6. With the patient wearing the prosthetic socket 1, two seals 26 would be directly superposed at their sealing edges 30.

The last-cited embodiment is especially appropriate for retrofitting when the prosthetic socket 1 on account of manufacturing methods does not subtend a sufficiently smooth surface in the vicinity around the aperture 38 that would be suitable for sealing using the sealing edge 30.

FIGS. 2 and 5 are based on the assumption that the sealing lip 28 was manufactured as a separate part. However it is quite clear that the sealing lip 28 also may be an integral part of the liner 3 on the outer side of same.

The shown above-knee socket serves merely an exemplary purpose. The invention is applicable to all kinds of prosthetic sockets such as below-knee and arm prostheses.

Summarizing, a prosthetic socket having an aperture at the distal end is fitted with a seal which is configured in a manner such that applying a tension to the prosthetic socket generates a self generating force at said seal, wherein the external atmospheric pressure increasingly compresses the seal through a sealing lip. The seal may be affixed to the prosthetic socket and/or to the liner, with the sealing edge always nearer the aperture to be sealed off than is the root of the sealing lip.

The invention claimed is:

1. A prosthetic liner for receiving a residual limb, the liner having a body with an open proximal end and a closed distal end, and an axis, the liner comprising:
    at least one seal having an annular sealing lip positioned about the body axis on the body distal end, the sealing lip including a root secured to the body distal end, and a sealing edge extending from the root towards the body axis, the sealing edge being biased away from the body distal end and forming an opening about the body axis.

2. The prosthetic liner according to claim 1, wherein the seal is configured as a disc-like annulus.

3. The prosthetic liner according to claim 1, wherein the seal is hermetically and adhesively bonded at the root to the liner body.

4. The prosthetic liner according to claim 1, wherein a compressible insert is provided between body distal end and the sealing edge.

5. The prosthetic liner according to claim 4, wherein the compressible insert is an open-pore foam or a spring.

6. The prosthetic liner according to claim 1, further comprising a locking element secured to the liner distal end and positioned along the body axis, the seal opening surrounding and radially spaced from the locking element.

7. The prosthetic liner according to claim 6, wherein the locking element is a pin having a serrated portion.

8. A prosthetic liner for receiving a residual limb, the liner having a body with an open proximal end and a closed distal end, and an axis, the liner comprising:
   at least one seal having an annular sealing lip positioned about the body axis on the body distal end, the sealing lip including a root secured to the body distal end, a first sealing edge extending from the root towards the body axis, and a second sealing edge extending from the root towards the body axis, the second sealing edge positioned more proximate to the liner distal end than the first sealing edge, the first and second sealing edges being biased away from the body distal end and forming an opening about the body axis.

9. The prosthetic liner according to claim 8, wherein the first and second edges are elastically maintained apart.

10. A prosthetic liner for receiving a residual limb, the liner having a body with an open proximal end and a closed distal end, the liner comprising:
    at least one seal having an annular sealing lip positioned obliquely relative to the body axis on the body distal end, the sealing lip including a root secured to the body distal end, and a sealing edge extending from the root, the sealing edge biased away from the body distal end and forming an opening.

11. The prosthetic liner according to claim 10, further comprising a locking element secured to the liner distal end, the seal opening surrounding and radially spaced from the locking element.

12. The prosthetic liner according to claim 11, wherein the locking element is an elongate cord.

* * * * *